United States Patent

Schmidt et al.

[11] 3,954,755
[45] May 4, 1976

[54] 7-BROMOQUINOXAL-6-YL-(THIONO)-(THIOL)-PHOSPHORIC AND (PHOSPHONIC) ACID ESTERS OF ESTER-AMIDES

[75] Inventors: Karl-Julius Schmidt, Wuppertal; Ingeborg Hammann, Cologne; Wilhelm Stendel, Wuppertal, all of Germany

[73] Assignee: Bayer Aktiengesellschaft, Leverkusen, Germany

[22] Filed: Mar. 3, 1975

[21] Appl. No.: 555,201

[30] Foreign Application Priority Data
Mar. 5, 1974  Germany............................ 2410311

[52] U.S. Cl............................. 260/250 QP; 424/200
[51] Int. Cl.²............................................ C07F 9/65
[58] Field of Search............................ 260/250 QP

[56] References Cited
FOREIGN PATENTS OR APPLICATIONS
1,160,493   8/1969   United Kingdom............... 260/250

*Primary Examiner*—Raymond V. Rush
*Assistant Examiner*—Mark L. Berch
*Attorney, Agent, or Firm*—Burgess, Dinklage & Sprung

[57] ABSTRACT

7-Bromoquinoxal(6)yl-(thiono)-(thiol)-phosphoric acid esters and ester-amides of the formula

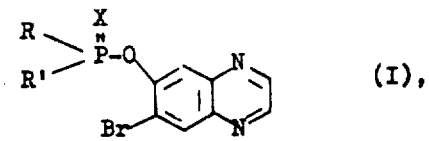

in which
R is alkoxy with 1 to 4 carbon atoms, alkyl with 1 to 3 carbon atoms or dialkylamino with 1 to 3 carbon atoms per alkyl moiety,
R' is alkoxy with 1 to 4 carbon atoms, alkylmercapto with 1 to 6 carbon atoms or dialkylamino with 1 to 3 carbon atoms per alkyl moiety, and
X is oxygen or sulfur,
which possess insecticidal and acaricidal properties.

7 Claims, No Drawings

7-BROMOQUINOXAL-6-YL-(THIONO)-(THIOL)-PHOSPHORIC AND (PHOSPHONIC) ACID ESTERS OF ESTER-AMIDES

The present invention relates to and has for its objects the provision of particular new 7-bromoquinoxal(6)-yl-(thiono) thiol-phosphoric acid esters and ester-amides which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DOS 1,670,817 and Belgian Patent Specification No. 702,672 that certain quinoxalyl-(thiono)-phosphoric-(phosphonic) acid esters, for example O,O-diethyl-O-3-bromo-quinoxal(2)-yl-phospheric acid ester (Compound A), O,O-diethyl-O-3-bromo-quinoxal(2)-yl-thionophosphoric acid ester (Compound B), and O,O-diethyl-O-quinoxal(6)-yl-phosphoric acid ester (Compound C), have insecticidal and acaricidal properties.

The present invention provides, as new compounds, the bromine-containing quinoxalyl-(thiono)-(thiol)-phosphoric (phosphonic) acid esters and ester-amides of the general formula

in which
R is alkoxy with 1 to 4 carbon atoms, alkyl with 1 to 3 carbon atoms or dialkylamino with 1 to 3 carbon atoms per alkyl moiety,
R' is alkoxy with 1 to 4 carbon atoms, alkylmercapto with 1 to 6 carbon atoms or dialkylamino with 1 to 3 carbon atoms per alkyl moiety, and X is oxygen or sulfur.

Preferably R is straight-chain or branched alkoxy with 1 to 3 carbon atoms, methyl, ethyl, dimethylamino or diethylamino, and R' is straight-chain or branched alkylmercapto with 1 to 5 carbon atoms (for example methylmercapto, ethylmercapto or n-propylmercapto), dimethylamino or diethylamino, or straight-chain or branched alkoxy with 1 to 3 carbon atoms (for example methoxy, ethoxy or propoxy).

Especially preferred compounds (I) are those in which R and R' are straight-chain or branched, identical or different alkoxy radicals with 1 to 3 carbon atoms; or in which R is straight-chain or branched alkoxy with 1 to 3 carbon atoms, and R' is straight-chain or branched alkylmercapto with 1 to 5 carbon atoms; or in which R is straight-chain or branched alkoxy with 1 to 3 carbon atoms and R' is dimethylamino or diethylamino; or in which R is methyl or ethyl and R' is straight-chain or branched alkoxy with 1 to 3 carbon atoms; or in which R is methyl or ethyl and R' is straight-chain or branched alkylmercapto with 1 to 5 carbon atoms; or in which R and R' are identical or different and are each dimethylamino or diethylamino.

Surprisingly, the bromine-containing quinoxalyl-(thiono)-(thiol)-phosphoric(phosphonic) acid esters and ester-amides according to the invention display a better insecticidal and acaricidal action than the previously known compounds of analogous structure and of the same type of action. They are not only active against insects and mites which damage plants but also against pests harmful to health and pests of stored products, and, in the veterinary medicine field, against ectoparasites, for example parasitic fly larvae. The compounds according to the invention thus represent a genuine enrichment of the art.

The invention also provides a process for the preparation of a bromine-containing quinoxalyl-(thiono)-(thiol)-phosphoric(phosphonic) acid ester or ester-amide of the formula (I), in which a (thiono)-(thiol)-phosphoric(phosphonic) acid ester halide or ester-amide halide or amide halide of the general formula

in which R, R' and X have the above-mentioned meanings, and Hal is halogen, preferably chlorine, is reacted, optionally in the presence of a diluent or solvent, with 6-hydroxy-7-bromo-quinoxaline of the formula

the latter compound being employed as such, and if appropriate in the presence of an acid acceptor, or in the form of a salt thereof, especially an alkali metal, alkaline earth metal or ammonium salt.

If 6-hydroxy-7-bromoquinoxaline and OO-ethyl-S-sec.-butylthiono-thiolphosphoric acid diester chloride are used as starting materials, the course of the reaction can be represented by the following equation:

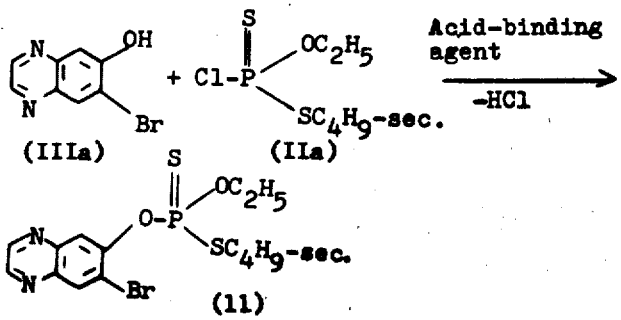

The (thiono)-(thiol)-phosphoric(phosphonic) acid ester halides, ester-amide halides and amide halides (II) which can be used in accordance with the process are described in the literature and can be prepared according to generally known processes.

The following may be mentioned individually as examples: O,O-diethyl-, O,O-dimethyl-, O,O-di-n-propyl-, O,O-di-isopropyl-, O,O-di-n-butyl-, O,O-di-sec.-butyl-, O,O-di-isobutyl-, O,O-di-tert.-butyl-, O-ethyl-O-n-propyl-, O-ethyl-O-isopropyl-, O-ethyl-O-sec.-butyl- and O-ethyl-O-tert.-butylphosphoric acid diester chlorides and the corresponding thiono analogues; O-methyl-S-methyl O-methyl-S-ethyl- O-methyl-S-n-propyl-, O-ethyl-S-ethyl-, O-ethyl-S-n-propyl-, O-ethyl-S-isopropyl-, O-ethyl-S-sec.-butyl-, O-ethyl-S-n-pentyl-, O-n-propyl-S-methyl-, O-n-propyl-S-ethyl-, O-n-propyl-S-ethyl-, O-n-propyl-S-n-propyl-, O-n-propyl-S-isopropyl, O-n-propyl-S-n-butyl-, O-n-propyl-S-tert.-butyl-, O-n-butyl-S-ethyl-, O-n-butyl-S-n-propyl-, O-n-butyl-S-n-butyl-, O-n-butyl-S-tert.-butyl- and O-n-butyl-S-n-pentyl-thiolphosphoric acid diester chlorides and the corresponding thiono analogues; O-methyl-, O-ethyl-, O-n-propyl-, O-isopropyl-, O-n-butyl-, O-isobutyl-, O-tert.-butyl- and O-sec.-butyl-methane- or -ethane or -propane-phosphonic acid ester chlorides, and S-methyl-, S-ethyl-, S-n-propyl-, S-iso-propyl-, S-n-butyl-, S-sec.-butyl-S-iso-butyl-, S-tert.-butyl- and S-n-pentyl-methane- or -ethane- or -propane-thiolphosphonic acid ester chlorides and the corresponding thiono analogues; and O-methyl-N,N-dimethyl-, O-methyl-N,N-diethyl-, O-ethyl-N,N-dimethyl-, O-ethyl-N,N-diethyl-, O-n-propyl-N,N-dimethyl-, O-n-propyl-N,N-diethyl-, O-n-butyl-N,N-dimethyl- and O-n-butyl-N,N-diethyl-phosphoric acid ester-amide chlorides, and also the corresponding diamides and the thiono analogues.

6-Hydroxy-7-bromoquinoxaline (III), to be used as a starting material, can be obtained from the known 6-hydroxyquinoxaline by halogenation, for example with bromine in water, in accordance with generally customary processes described in the literature.

The process for the preparation of the compounds according to the invention is preferably carried out in the presence of a suitable solvent or diluent. Practically all inert organic solvents can be used for this purpose, especially aliphatic and aromatic, optionally chlorinated hydrocarbons, such as benzene, toluene, xylene, benzine, methylene chloride, chloroform, carbon tetrachloride or chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as the acid acceptors. Alkali metal carbonates and alkali metal alcoholates, such as sodium carbonate, potassium carbonate, sodium methylate, potassium methylate, sodium ethylate and potassium ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 10° and 120°C, preferably at from 40° to 80°C.

To carry out the process, the starting materials are in general employed in equimolar amounts. An excess of one or the other reactant in general produces no significant advantages. The reaction is preferably carried out in the process of one of the above-mentioned solvents, if appropriate in the presence of an acid acceptor, at the temperatures indicated. After a reaction time of one or more hours, in most cases at an elevated temperature, the batch is cooled and the reaction mixture is poured into water and taken up in an organic solvent, for example benzene. The reaction mixture is then worked up in the usual manner by drying the organic phase and evaporating the solvent.

The new compounds are in some cases obtained in the form of oils which mostly cannot be distilled without decomposition but can be freed from the last volatile constituents by so-called "slight distillation," that is to say by prolonged heating under reduced pressure to moderately elevated temperatures, and can be purified in this way. They are characterized by the refractive index. Some of the compounds are obtained in a crystalline form of sharp melting point.

As has already been mentioned, the bromine-containing quinoxalyl-(thiono)-(thiol)-phosphoric(phosphonic) acid esters and ester-amides according to the invention are distinguished by an outstanding insecticidal and acaricidal activity. They are active against plant pests, pests harmful to health and pests of stored products and, in the veterinary medicine field, against animal parasites (ectoparasites), such as parasitic fly larvae. They have a low phytotoxicity and a good action against sucking and biting insects.

For this reason, the compounds according to the inventon can be employed successfully as pesticides in plant protection as well as in the hygiene field, the field of protection of stored products and the veterinary field.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Neophotettix bipunctatus*.

In the case of the biting insects, above all there should be mentioned butterfly caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermina moth (*Hyponomeuta padella*), the Mediterranean flour moth (Ephestia kuhniella) and greater wax moth (*Galleria mellonella*).

Also to be classed with the biting insects are beetles (*Coleoptera*), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, *Orthoptera*, for example the house cricket (*Gryllus domesticus*); termites such as the eastern subterranean termite (*Reticulitermes flavipes*) and *Hymenoptera* such as ants, for example the garden ant (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly *Calliphora erythrocephala*) as well as the stable fly (*Stomoxys calcitrans*); further gnats, for example mosquitoes such as the yellow fever mosquito (*Aedes aegypti*), the northern house mosquito (*Culex pipiens*) and the malaria mosquito (*Anopheles stephensi*).

With the mites (*Acarina*) there are classed, in particular, the spider mites (*Tetranychidae*) such as the two-spotted spider mite (*Tetranychus urticae*) and the European red mite (*Paratetranychus pilosus* = *Panonychus ulmi*), gall mites, for example the blackcurrent gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as a conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application of field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. a nematocidally, insecticidally, acaricidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed.

The active compounds, the concentrations of the active compounds, the evaluation times and the degree of destruction can be seen from the following table:

Table 1

| Active compounds | Active compound concentration in % | Degree of destruction in % after 1 day |
|---|---|---|
| (insects which damage plants) *Drosophila* test | | |
| 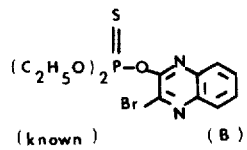 (known) (B) | 0.1<br>0.01 | 100<br>0 |
| 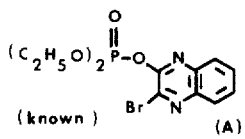 (known) (A) | 0.1<br>0.01 | 100<br>0 |
| 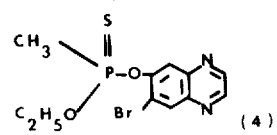 (4) | 0.1<br>0.01 | 100<br>100 |

Table 1-continued (insects which damage plants)
Drosophila test

| Active compounds | Active compound concentration in % | Degree of destruction in % after 1 day |
|---|---|---|
| 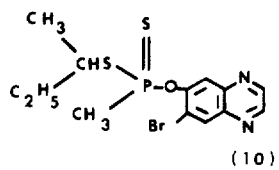 (10) | 0.1<br>0.01 | 100<br>100 |
| 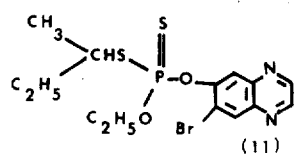 (11) | 0.1<br>0.01<br>0.001 | 100<br>100<br>100 |

EXAMPLE 2

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed, whereas 0% means that none of the caterpillars were killed.

The active compounds, the concentrations of the active compounds, the evaluation times and the results can be seen from the following table:

Table 2

(insects which damage plants)
Plutella test

| Active compounds | Active-compound concentration in % | Degree of destruction in % after 3 days |
|---|---|---|
| 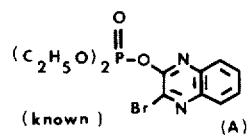 (known) (A) | 0.1<br>0.01<br>0.001 | 100<br>85<br>0 |
| 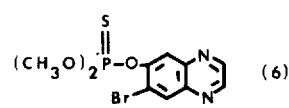 (6) | 0.1<br>0.01<br>0.001 | 100<br>100<br>100 |
| 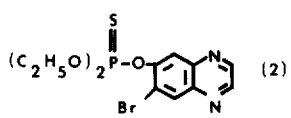 (2) | 0.1<br>0.01<br>0.001 | 100<br>100<br>80 |

Table 2-continued (insects which damage plants)
*Plutella* test

| Active compounds | Active-compound concentration in % | Degree of destruction in % after 3 days |
|---|---|---|
| 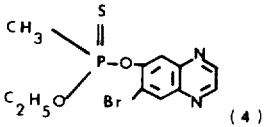 (4) | 0.1<br>0.01<br>0.001 | 100<br>100<br>95 |
| 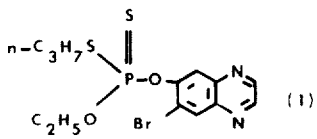 (1) | 0.1<br>0.01<br>0.001 | 100<br>100<br>100 |

EXAMPLE 3

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed, whereas 0% means that none of the aphids were killed.

The active compounds, the concentrations of the active compounds, the evaluation times and the results can be seen from the following table:

Table 3

(insects which damage plants)
*Myzus* test

| Active compounds | Active compound concentration in % | Degree of destruction in % after 1 day |
|---|---|---|
| 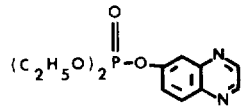<br>(known) (C) | 0.1<br>0.01<br>0.001 | 100<br>70<br>30 |
| 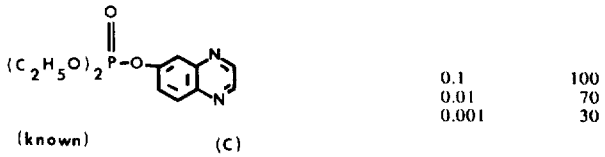<br>(known) (B) | 0.1 | 0 |

Table 3-continued

| Active compounds | (insects which damage plants) Myzus test | Active compound concentration in % | Degree of destruction in % after 1 day |
|---|---|---|---|
| (structure 5): (CH₃)₂CHO, CH₃, Br-quinoxalinyl-O-P(=S) | | 0.1<br>0.01<br>0.001 | 100<br>100<br>99 |
| (structure 10): (CH₃)₂CHS, C₂H₅, CH₃, Br-quinoxalinyl-O-P(=S) | | 0.1<br>0.01<br>0.001 | 100<br>100<br>95 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10-30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following table:

Table 4

| Active compounds | (mites which damage plants) Tetranychus test | Active compound concentration in % | Degree of destruction in % after 2 days |
|---|---|---|---|
| 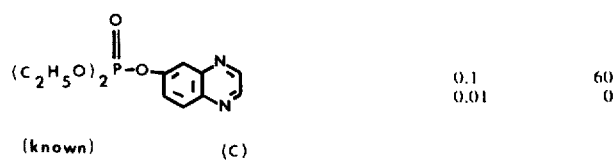 (known) (C) | | 0.1<br>0.01 | 60<br>0 |
| 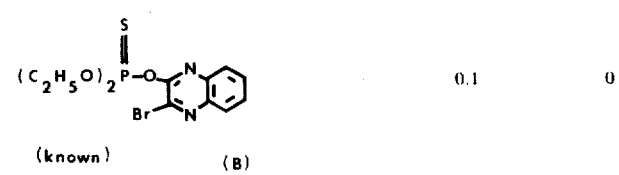 (known) (B) | | 0.1 | 0 |

Table 4-continued
(mites which damage plants)
*Tetranychus* test
| Active compounds | Active compound concentration in % | Degree of destruction in % after 2 days |
|---|---|---|
| 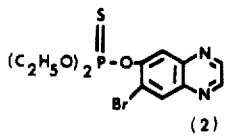 (2) | 0.01<br>0.01 | 95<br>75 |
| 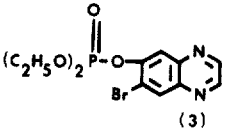 (3) | 0.01<br>0.01 | 95<br>80 |
| 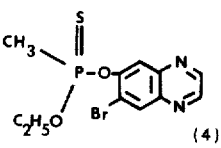 (4) | 0.01<br>0.01 | 100<br>98 |
| 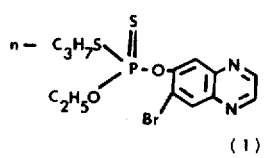 (1) | 0.01<br>0.01 | 100<br>100 |
| 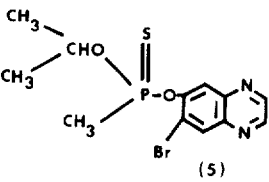 (5) | 0.1<br>0.01 | 100<br>100 |
| 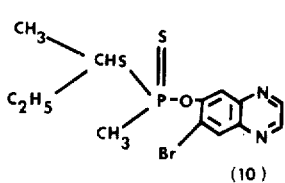 (10) | 0.1<br>0.01 | 100<br>100 |
EXAMPLE 5
Test with parasitic fly larvae
Solvent: 35 parts by weight of ethylene polyglycol monomethyl ether
35 parts by weight of nonylphenol polyglycol ether To produce a suitable preparation of active compound, 30 parts by weight of the active substance in question were mixed with the stated amount of solvent which contains the above-mentioned proportion of emulsifier and the concentrate thus obtained was diluted with water to the desired concentration.

About 20 fly larvae (*Lucilia cuprina*) were introduced into a test tube which contained about 2 ml of horse muscle. 0.5 ml of the preparation of active compound was applied to this horse meat. After 24 hours, the degree of destruction in % was determined. 100% means that all the larvae had been killed and 0% means that no larvae had been killed.

This gave 83 g (66% of theory) of 6-hydroxy-7-bromo-quinoxaline of melting point 176°C (with decomposition).

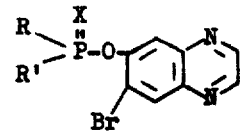

(1)

A mixture of 45 g (0.2 mole) of 6-hydroxy-7-bromoquinoxaline and 30 g of potassium carbonate in 300 ml of acetonitrile was warmed to 80°C for 30 min- Table 5

| Active compound | Concentration in ppm | Degree of destruction in % *Lucilia cuprina* res. |
|---|---|---|
| (1) | 10,000 | 100 |
| | 100 | 100 |
| | 30 | 100 |
| | 10 | 100 |
| | 3 | 100 |
| (6) | 10,000 | 100 |
| | 100 | 100 |
| | 30 | 100 |
| | 10 | 100 |
| | 3 | 100 |

The process of this invention is illustrated by the following preparative Examples.

EXAMPLE 6 a. 6Hydroxy-7-bromo-quinoxaline, used as a starting material, is obtained as follows:

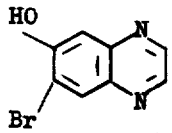

(III)

80 g of bromine were added to 73 g (0.5 mole) of 6-hydroxy-quinoaxaline in 300 ml of water at a temperature of 20° to 50°C. The reaction mixture was stirred for a further 2 hours at the stated temperature; it was then cooled and the product was filtered off. The precipitate was dissolved in sodium hydroxide solution, reprecipitated with hydrochloric acid and filtered off. The residue was washed with water and dried in air.

utes and 44 g (0.2) mole) of 0-ethyl-S-n-propyl-thiono-thiolphosphoric acid diester chloride were then added, while keeping the slightly exothermic reaction at a temperature of between 40° and 50°C. After boiling for 3 hours, the reaction mixture was poured into water and taken up in toluene, and the organic phase was washed with water. After drying over sodium sulfate, the mixture was evaporated and the residue was subjected to "slight distillation." 38 g of 0-ethyl-0-[7-bromoquinoxal(6)yl]-S-n-propyl-thionothiolphosphoric acid ester having a refractive index $n_D^{22}$ of 1.6235 were thus obtained.

The following compounds of the formula (I)

were prepared analogously:

Table 6

| Compound No. | R | R' | X | Physical data |
|---|---|---|---|---|
| 2 | —OC₂H₅ | —OC₂H₅ | S | melting point 101°C |
| 3 | —OC₂H₅ | —OC₂H₅ | O | melting point 91–92°C |
| 4 | —CH₃ | —OC₂H₅ | S | melting point 104–105°C |
| 5 | —CH₃ | —OC₃H₇-iso | S | melting point 99–100°C |
| 6 | —OCH₃ | —OCH₃ | S | melting point 91°C |
| 7 | —N(CH₃)₂ | —N(CH₃)₂ | O | melting point 106°C |
| 8 | —OC₂H₅ | —SCH₃ | S | melting point 67°C |
| 9 | —OC₂H₅ | —SC₂H₅ | S | melting point 53°C |
| 10 | —CH₃ | —S—CH—C₂H₅<br>CH₃ | S | $n_D^{24}$ : 1.6457 |

Table 6-continued

| Compound No. | R | R' | X | Physical data |
|---|---|---|---|---|
| 11 | —OC$_2$H$_5$ | —S—CH—C$_2$H$_5$ | S | n$_D^{24}$: 1.6381 |

It will be appreciated that the instant specification and examples are set forth by way of illustration and not limitation, and that various modifications and changes may be made without departing from the spirit and scope of the present invention.

What is claimed is:

1. A 7-bromoquinoxal(6)yl-(thiono)-(thiol)-phosphoric (phosphonic) acid ester or ester-amide of the formula

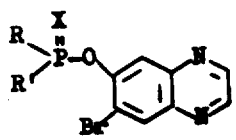

in which
R is alkoxy with 1 to 4 carbon atoms, alkyl with 1 to 3 carbon atoms or dialkylamino with 1 to 3 carbon atoms per alkyl moiety,
R' is alkoxy with 1 to 4 carbon atoms, alkylmercapto with 1 to 6 carbon atoms or dialkylamino with 1 to 3 carbon atoms per alkyl moiety, and
X is oxygen or sulfur.

2. A compound according to claim 1, in which R is straight-chain or branched alkoxy with 1 to 3 carbon atoms, methyl, ethyl, dimethylamino or diethylamino, and R' is straight-chain or branched alkylmercapto with 1 to 5 carbon atoms, dimethylamino or diethylamino, or straight-chain or branched alkoxy with 1 to 3 carbon atoms.

3. The compound according to claim 1 wherein such compound is 0-ethyl-0-[7-bromoquinoxal(6yl)]-S-n-propyl-thionothiolphosphoric acid ester of the formula

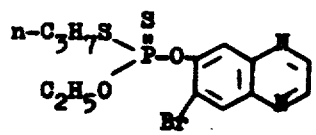

4. The compound according to claim 1 wherein such compound is 0-ethyl-0-[7-bromoquinoxal(6)yl]-methanethionophosphonic acid ester of the formula

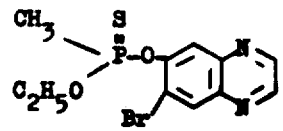

5. The compound according to claim 1 wherein such compound is 0,0-dimethyl-0-[7-bromoquinoxal(6)yl]-thionophosphoric acid ester of the formula

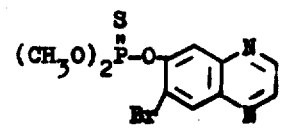

6. The compound according to claim 1 wherein such compound is 0-[7-bromoquinoxal(6)-S-sec.-butylmethanethionothiolphosphonic acid ester of the formula

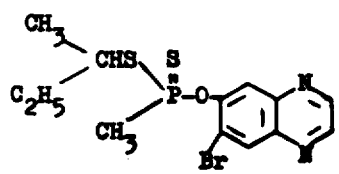

7. The compound according to claim 1 wherein such compound is 0-isopropyl-0-[7-bromoquinoxal(6)yl]-methanethionophosphonic acid ester of the formula

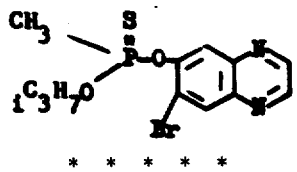

* * * * *